United States Patent
Piriou et al.

(10) Patent No.: US 9,879,287 B2
(45) Date of Patent: Jan. 30, 2018

(54) PROCESS FOR DRY FRACTIONATION OF LIGNOCELLULOSIC BIOMASS

(71) Applicants: INSTITUT NATIONAL DE LA RECHERCHE AGRONOMIQUE, Paris (FR); CIRAD (CENTRE DE COOPÉRATION INTERNATIONALE EN RECHERCHE AGRONOMIQUE POUR LE DÉVELOPPEMENT, Paris (FR)

(72) Inventors: Bruno Piriou, Montpellier (FR); Abdellatif Barakat, Montpellier (FR); Xavier Rouau, Montpellier (FR); Gilles Vaitilingom, Claret (FR)

(73) Assignees: INSTITUT NATIONAL DE LA RECHERCHE AGRONOMIQUE, Paris (FR); CIRAD, Paris (FR)

(*) Notice: Subject to any disclaimer, the term of this patent is extended or adjusted under 35 U.S.C. 154(b) by 62 days.

(21) Appl. No.: 15/106,988

(22) PCT Filed: Dec. 24, 2014

(86) PCT No.: PCT/EP2014/079333
§ 371 (c)(1),
(2) Date: Jun. 21, 2016

(87) PCT Pub. No.: WO2015/097298
PCT Pub. Date: Jul. 2, 2015

(65) Prior Publication Data
US 2016/0369305 A1  Dec. 22, 2016

(30) Foreign Application Priority Data
Dec. 24, 2013 (FR) ........ 13 63543

(51) Int. Cl.
*C12P 7/10* (2006.01)
*B02C 23/08* (2006.01)
(Continued)

(52) U.S. Cl.
CPC ........ *C12P 7/10* (2013.01); *B02C 23/08* (2013.01); *B03C 7/006* (2013.01); *C01B 3/02* (2013.01);
(Continued)

(58) Field of Classification Search
CPC ........................................ C12P 7/10
See application file for complete search history.

(56) References Cited

U.S. PATENT DOCUMENTS

| 5,944,875 A | 8/1999 | Stencel et al. | |
|---|---|---|---|
| 2015/0007492 A1* | 1/2015 | Piriou | C10L 5/44 44/505 |

FOREIGN PATENT DOCUMENTS

| DE | 10 2008 047899 A1 | 3/2010 |
|---|---|---|
| DE | 10 2012 203148 B3 | 8/2013 |

(Continued)

OTHER PUBLICATIONS

Arakat et al., "Eco-friendly dry chemo-mechanical pretreatments of lignocellulosic biomass: Impact on energy and yield of the enzymatic hydrolysis," Applied Energy, 2014, pp. 97-105, vol. 113, Elsevier Ltd.

*Primary Examiner* — Melvin C Mayes
*Assistant Examiner* — Stefanie Cohen
(74) *Attorney, Agent, or Firm* — Im IP Law; C. Andrew Im (57) ABSTRACT

The process for the dry fractionation of lignocellulosic biomass of at least 50% by weight of lignins, cellulose and hemicelluloses. The biomass is fragmented to obtain an ultrafine powder. The process includes at least one step of (Continued)

separating a fraction enriched with cellulose and a fraction enriched with lignin, hemicelluloses and minerals by electrostatic sorting of the ultrafine particles. Preferably, the fraction separation step includes a step of triboelectrostatic charging of ultrafine particles and at least one step of deviating a path in the electric field of the charged particles to sort the particles.

19 Claims, 8 Drawing Sheets

(51) Int. Cl.
| | | |
|---|---|---|
| *B03C 7/00* | (2006.01) | |
| *C01B 3/02* | (2006.01) | |
| *C10L 1/02* | (2006.01) | |
| *C10L 3/08* | (2006.01) | |
| *C10L 5/36* | (2006.01) | |
| *C10L 5/44* | (2006.01) | |
| *C12P 3/00* | (2006.01) | |
| *C12P 5/02* | (2006.01) | |
| *C12P 19/02* | (2006.01) | |
| *C12P 19/14* | (2006.01) | |

(52) U.S. Cl.
CPC .................................. *C10L 1/02* (2013.01); *C10L 3/08* (2013.01); *C10L 5/366* (2013.01); *C10L 5/44* (2013.01); *C12P 3/00* (2013.01); *C12P 5/023* (2013.01); *C12P 19/02* (2013.01); *C12P 19/14* (2013.01); *C10L 2200/0469* (2013.01); *C10L 2290/26* (2013.01); *C10L 2290/28* (2013.01); *C10L 2290/54* (2013.01); *C12P 2201/00* (2013.01); *Y02E 50/10* (2013.01); *Y02E 50/16* (2013.01); *Y02E 50/30* (2013.01); *Y02E 50/343* (2013.01); *Y02P 20/582* (2015.11); *Y02P 30/20* (2015.11)

(56) References Cited

FOREIGN PATENT DOCUMENTS

EP 0 330 462 A2 8/1989
FR 2 985 735 A1 7/2013

\* cited by examiner

PROCESS FOR DRY FRACTIONATION OF LIGNOCELLULOSIC BIOMASS

RELATED APPLICATIONS

This application is a §371 application from PCT/EP2014/079333 filed Dec. 24, 2014, which claims priority from French Patent Application No. 13 63543 filed Dec. 24, 2013, each of which is incorporated herein by reference in its entirety.

TECHNICAL FIELD OF THE INVENTION

The present invention relates to a dry process for the fractionation of lignocellulosic biomass. It applies in particular to the obtaining of fractions enriched in cellulose, hemicelluloses, lignin, inorganics and/or other advantageous constituents.

STATE OF THE ART

The available biomasses comprise in particular agricultural coproducts (such as straw, stalks and leaves) and food-processing coproducts (shells, chaff, husks, skins), wood (in particular in the form of cutting products, leaf, bark, chips and sawdust), energy crops, for example short rotation coppice, annual and perennial plants, grasses, packaging and organic waste and dried fresh products, terrestrial and aquatic plants.

Processes for the refining of lignocellulosic biomass contribute to the provision of bioenergies, in the form of powder and of ethanol, of biobased materials, in particular for being fillers in matrices, and of biomolecules having high added value, for example phenols, fatty acids and inorganics.

The known physical or chemical processes use steps of compression and of intense washing with water and with organic solvents, in order to recover the lignin, cellulose and hemicelluloses. These techniques are very expensive in capital costs and in energy. They have a very high impact on the economics of the process and on the environment. Furthermore, these processes are not well suited to the extraction of lignin, on account of their cost and owing to the fact that the lignins extracted are often modified or contaminated by chemical reactants (sulfates, acetyls, and the like) and undergo depolymerization/repolymerization reactions which make it more difficult to give them economic value. Furthermore, the need for a complete recycling of the reactants is economically damaging to processes of this type.

In the chemical processes (extraction by solvent, in an acidic or alkaline medium, and the like), the functionalities of the biopolymers (lignins and polysaccharides, such as cellulose and hemicelluloses) are detrimentally effected or modified by secondary oxidation and hydrolysis reactions, which is damaging to their subsequent uses. Furthermore, in these processes, steps expensive in energy and in capital costs are necessary (neutralizations, purifications, drying, recycling and treatments of waste, and the like).

The document EP 0 330 462 describes an example of application of a fraction resulting from biomass. This fraction is enriched in silica and other materials present in rice hull ash.

The document FR 2 985 735, which describes a process for the preparation of a lignocellulose constituent in the form of a powder is known. This process comprises several grinding steps, optionally separated by a step of removal of the smaller particles, the final step thus always being a grinding step. This process thus only provides a single fraction of the initial sample.

SUBJECT MATTER OF THE INVENTION

The present invention aims to remedy all or some of these drawbacks.

To this end, according to a first aspect, the present invention relates to a dry process for the fractionation of lignocellulosic biomass comprising at least 50% by weight of lignins, cellulose and hemicelluloses, which process comprises:
- a step of fragmenting the biomass in order to obtain an ultrafine powder and
- at least one step of separating a fraction enriched in cellulose, on the one hand, and a fraction enriched in lignin and in hemicelluloses, on the other hand, by electrostatic sorting of the ultrafine particles.

Subsequent operations of aerodynamic sorting (based on the density of the particles) and of dimensional sorting (based on the size of the particles) can be applied to the previously separated fractions, in order to increase their purity.

The process which is a subject matter of the present invention makes it possible to concentrate the lignins, inorganics and polysaccharides without solvent, without chemical reactant and without recycling and treatment of the wastes. This process thus makes it possible to very effectively enhance in economic value these various fractions to give biobased materials and biomolecules.

A biobased product is a non-foodstuff partially or completely resulting from the biomass. Biobased products include high-value products, such as those resulting from fine chemistry (pharmaceuticals, fragrances, food additives, and the like), and also specialty products (lubricants, detergents, and the like), or also commodity products (polymers, chemical intermediates, and the like). The concept excludes conventional biobased products, such as those which originate from pulp and paper, wood and biomass, used as energy source. Reference is made to biobased products for a wide range of applications and to biobased material more specifically in the field of ecoconstruction.

The term "ultrafine powder" is understood to mean here a set of particles, the median diameter (d50) of which is less than 200 μm (50% of the total volume of the particles corresponds to the volume of particles with diameters of less than d50). The homogeneity of the composition of the particles resulting from the grinding of plants increases when their size decreases. Thus, some ultrafine particles exhibit a high content of lignins, cellulose and/or hemicelluloses. It should be noted that these lignins, cellulose and hemicelluloses are present in the walls of the plants.

The combination of the steps of ultrafine grinding (particles with a d50 of less than 200 μm) of the lignocelluloses (wood and coproducts of the industry, agricultural and food-processing coproducts, dedicated plants, municipal and industrial waste) and of sorting in a strict dry medium (electrostatic sorting, dimensional sorting, aerodynamic sorting) makes it possible to isolate fractions enriched in cellulose, in hemicelluloses, in lignins and/or in inorganics, without chemical modification, in contrast to the chemical fractionation processes developed to date.

In embodiments, the step of sorting of ultrafine particles comprises:
- a step of triboelectrostatically charging ultrafine particles and
- at least one step of deviating the path of the charged particles in the electric field in order to sort the particles.

The inventors have determined that this type of sorting is particularly effective.

In embodiments, the process which is a subject matter of the present invention additionally comprises a step of scraping an electrode of an electrostatic sorting means used during the deviating step, so as to collect the particles attached to an electrode after the particles deviating step.

These embodiments make it possible to collect the particles attached to the electrode, the electric charge of which is strong, which means that their composition is particularly homogeneous.

In embodiments, the process which is a subject matter of the present invention additionally comprises a step of cyclically reversing the polarity of each electrode of an electrostatic sorting means used during the deviating step.

These embodiments make it possible to detach and collect the particles attached to the electrodes, the compositions of which are particularly homogeneous, and to collect the particles attached to each electrode without mechanical action, such as scraping.

In embodiments, the process which is a subject matter of the present invention comprises, downstream of the deviating step, at least one secondary deviating step.

The separation of the components resulting from the plurality of successive sortings carried out by the process is then more precise.

In embodiments, the least charged particles obtained after a first deviating step are recycled in the triboelectrostatic separator.

The advantage of these embodiments is that they allow the particles, the electric charge of which is indeterminate after two electrostatic sortings, to follow a further implementation of the process of the present invention.

In embodiments, the process which is a subject matter of the present invention comprises, downstream of at least one deviating step, a step of comparing the sizes of the particles with a predetermined limit value and a step of feeding a grinding means with particles the sizes of which are greater than the predetermined limit.

By virtue of these arrangements, particles which are too large to be efficiently sorted are ground again so as to optimize their sorting. On the other hand, the particles, the dimensions of which are nominal, can be sorted again without undergoing additional grinding.

In embodiments, during the charging step, a dynamic fluidized air bed is used.

The use of a fluidized air bed makes possible simultaneously the formation of electrostatic charges on the moving particles and their separation for the purpose of their sorting.

In embodiments, during the step of fragmenting the biomass, a grinding of the biomass is carried out.

In embodiments, during the step of fragmenting the biomass, a vibrating mill or a rotary ball mill is employed.

In embodiments, the process which is the subject matter of the present invention comprises, upstream of or during the step of fragmenting the biomass, a step of pretreatment of the biomass.

This pretreatment makes it possible to promote the deconstruction of the biomass during the grinding.

In embodiments, during the pretreatment step, a chemical treatment of the biomass is carried out by contact with an oxidizing gas or aerosol.

For example, an oxidizing gas comprising oxygen or ozone can be used. Oxidizing agents are known to bring about the decomposition of the phenolic constituents of the plant wall and thus promote breaking under mechanical stress.

In embodiments, during the pretreatment step, a chemical treatment of the biomass is carried out by contact with a reducing gas or aerosol.

In embodiments, during the pretreatment step, a chemical treatment of the biomass is carried out by contact with an inert gas.

In embodiments, during the pretreatment step, the inert gas is nitrogen.

In embodiments, the process which is a subject matter of the present invention comprises, downstream of the separating step, a step of functionalizing at least one enriched fraction.

In embodiments, during the functionalizing step, a roasting of the enriched fraction is carried out.

In embodiments, during the functionalizing step, an enzymatic hydrolysis of the enriched fraction is carried out.

The present invention relates, according to a second aspect, to a use of the process which is a subject matter of the present invention for generating biofuel from components enriched in lignocellulose and/or depleted in inorganics.

It should be remembered here that a biofuel is a fuel produced from nonfossil organic materials originating from the biomass and which supplements or replaces fossil fuels. Biofuels comprise in particular biohydrogen, bioethanol, biomethane and biopowders, or solid fuel.

The present invention relates, according to a third aspect, to a use of the process which is a subject matter of the present invention for obtaining fractions participating in the manufacture of biobased materials, such as, for example, particles acting as fillers in polymer matrices, making it possible to adjust their properties (mechanical properties, permeability, and the like).

The present invention relates, according to a fourth aspect, to an enriched fraction resulting from the process which is a subject matter of the present invention.

As the specific advantages, aims and characteristics of these applications and fraction which are subject matters of the present invention are similar to those of the process which is a subject matter of the present invention, they are not recalled here.

BRIEF DESCRIPTION OF THE FIGURES

Other specific advantages, aims and characteristics of the invention will emerge from the nonlimiting description which follows of at least one specific embodiment of the fractionation device and process which are subject matters of the present invention, with regard to the appended drawings, in which.

DESCRIPTION OF IMPLEMENTATION EXAMPLES OF THE INVENTION

The present description is given in a non limiting manner.

It should be immediately noted that the figures are not to scale.

The term "ultrafine" refers to a powder, the particles of which have a median diameter of less than 200 micrometers, preferably between 10 micrometers and 200 micrometers.

According to another definition, the term "ultrafine" refers to a powder of which half (50%) by volume of the particles have a dimension of less than 200 micrometers (d50<200 µm), preferably of less than 100 micrometers and more preferably of less than 50 micrometers.

A laser particle size analyzer can be used to measure the particles.

The dry refining of the plant has the aim of rendering the biomass and in particular the lignocellulosic biomass more suitable for a given final use. Processes of this type have the distinguishing feature of not generating polluting effluents, in contrast to liquid refining.

Figure 1:
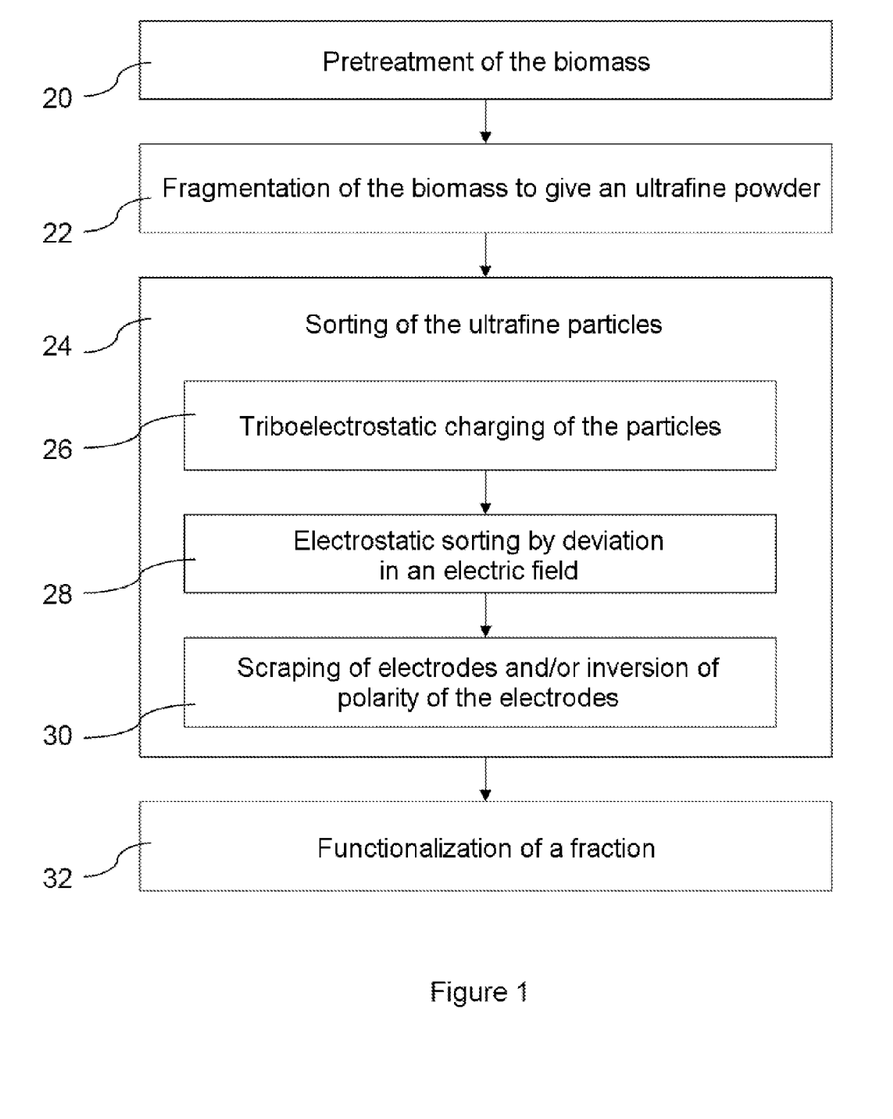
FIG. 1 represents, in the form of a logic diagram, steps of a specific embodiment of the process which is a subject matter of the present invention.

A specific embodiment of the dry process for the fractionation of lignocellulosic biomass which is a subject matter of the present invention is observed in FIG. 1. This process comprises, in order to separate a fraction enriched in cellulose from a fraction enriched in lignin and hemicelluloses:
- a step 20 of pretreatment of the biomass;
- a step 22 of fragmenting the biomass in order to obtain an ultrafine powder;
- at least one step 24 of sorting the ultrafine particles by electrostatic sorting. The fractions resulting from this step can subsequently be subjected to optional steps of aerodynamic sorting and/or of dimensional sorting in order to improve their purity.
- an optional step 32 of functionalizing at least one sorted fraction.

The object of the step 20 of pretreatment of the biomass and of the lignocellulosic biomass in particular is to modify its surface or bulk physicochemical composition in order to render it more suitable for the steps which follow. It can be a matter of reducing the grinding costs by rendering the biomass weaker. It can also be a matter of increasing the reactivity.

The pretreatment step 20 preferably promotes the deconstruction of the biomass during the step 22 of fragmenting the biomass. In embodiments, during the pretreatment step 20, a chemical treatment is carried out by the gas, aerosol or vapor route, in particular a chemical pretreatment consisting in treating the biomass with an oxidizing gas or aerosol.

For example, an oxidizing gas comprising oxygen or ozone can be used and brings about the decomposition of the phenolic constituents of the plant wall and thus promotes breaking under mechanical stress.

In embodiments, during the pretreatment step 20, the biomass is treated with a reducing gas or aerosol.

Figure 10:
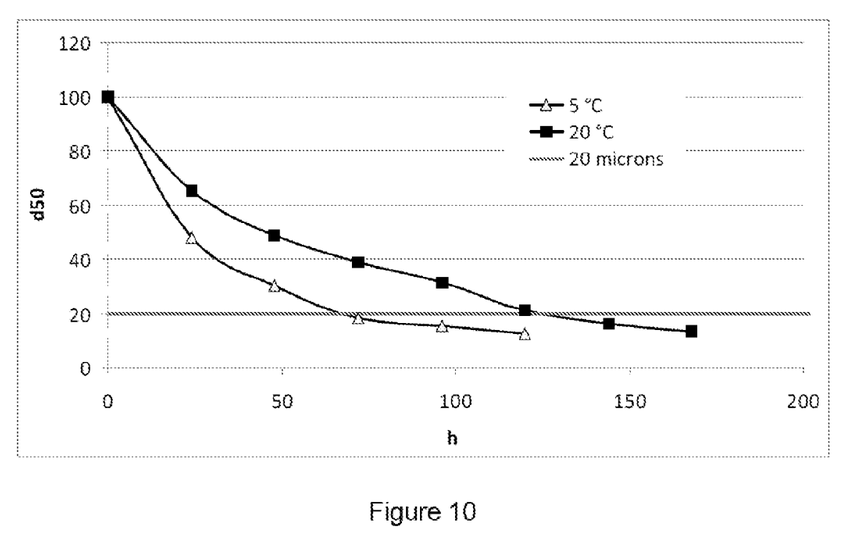
FIG. 10 shows, on two curves, the change in the duration of grinding when the biomass is cooled during grinding.

In embodiments, during the pretreatment step 20, the biomass is cooled (see FIG. 10).

In embodiments, during the step 22 of fragmenting the biomass, a grinding of the biomass is carried out. For example, a vibrating mill or rotary ball mill is employed.

It should be noted that, in embodiments, the pretreatment step 20 is simultaneous with the step 22 of fragmenting the biomass.

In the embodiment represented in FIG. 1, the step 24 of sorting the ultrafine particles comprises:
- a step 26 of triboelectrostatically charging ultrafine particles,
- at least one step 28 of electrostatic sorting by deviating the path of the charged particles in the electric field, in order to sort the particles, and
- a step 30 of scraping at least one electrode of an electrostatic sorting means used during the deviating step in order to collect the particles attached to an electrode after the particle deviating step.

The step 26 of triboelectrostatic charging is carried out, for example, by the collision between the particles and an internal surface of a pipe comprising a part made of PVC, Teflon and/or glass and steel, for example by the use of an air bed ventilated by virtue of a turbine or a fan, for example. In particular, the particles comprising fractions enriched in lignocellulose become positively charged during the step 26. This fluidized air bed moves the particles in order to carry out the charging step 26 and moves these charged particles up to an electrostatic sorting means.

In embodiments, the scraping step 30 is supplemented or replaced by a step (not represented) of cyclically reversing the polarity of each electrode of an electrostatic sorting means used during the deviating step. By virtue of the scraping or of the polarity inversion, the particles attached to each electrode are detached and collected.

Each step 28 of electrostatic sorting is carried out by deviating the path of the charged particles in the electric field produced between two electrodes. The particles comprising fractions enriched in cellulose are attracted by a negatively polarized electrode and the particles enriched in lignin and hemicelluloses and inorganics are attracted by a positively polarized electrode, during the step 28.

Preferably, the step 28 of path deviating comprises two successive steps of path deviating, primary and secondary, in two electrostatic sorting means arranged in series. The separation of the components resulting from the plurality of successive sortings carried out by the process is then more precise.

In embodiments, at the outlet of a secondary deviating step, a triboelectrostatic charging means is fed with particles which have not been separated after two sorting steps (collected in the central containers). The advantage of these embodiments is that they make it possible for the particles, the net electric charge of which does not make possible separation after two electrostatic sortings, to follow a further implementation of the process which is a subject matter of the present invention.

In embodiments, the process which is a subject matter of the present invention comprises, downstream of at least one deviating step, a step of comparing the dimensions of particles compared with a predetermined limit value and the particles, the dimensions of which are greater than the predetermined limit, are returned to the grinding step. Thus, the particles which are too large to be efficiently sorted are ground again so as to optimize their sorting. On the other hand, the particles, the dimensions of which are nominal, can be sorted again without being subjected to additional grinding.

In embodiments, during the charging step 26, a dynamic fluidized air bed is employed. This fluidized air bed makes possible simultaneously the forming of the electrostatic charges on the moving particles and their separation for the purpose of their sorting.

The step 32 of functionalizing at least one fraction of sorted particles comprises, for example, a roasting step which makes it possible to densify the energy content of the particles and to promote their flow properties.

Figure 2:
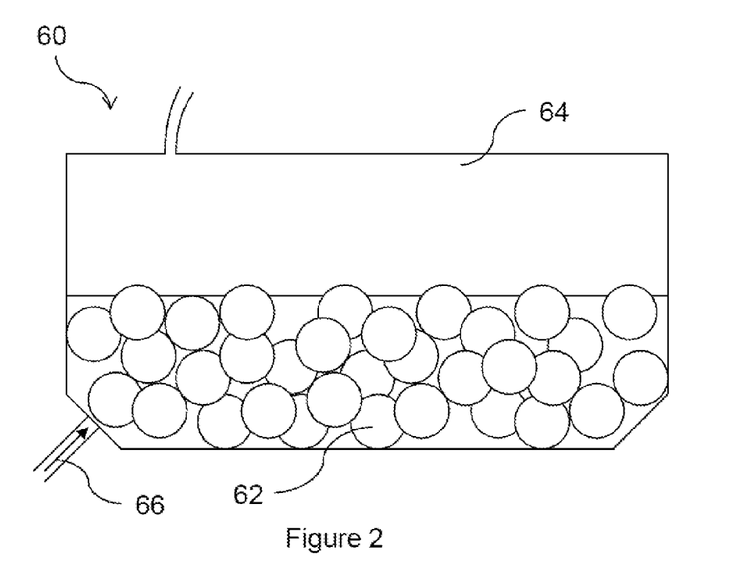
FIG. 2 represents, diagrammatically and in section, a means for dry pretreatment with a gas.

A means for the dry pretreatment 60 of biomass is observed in FIG. 2. In this means, the lignocellulose material is brought into contact with a gas having specific properties (oxidizing or reducing, and so on), in order to modify its fragmentability or its reactivity. A vibrating ball mill 62 make possible access to the product during grinding, so that a continuous and controlled flushing of gas 66 through the product can be carried out. Likewise, the filling of the vessel 64 makes it possible to keep the amount of gas in the vessel 64 constant throughout the grinding.

Among the gases which can be used, inert gases can modify the surface oxidation state of the lignocellulose material and its reactivity (argon, nitrogen, $CO_2$).

Among the gases which can be used, oxidizing gases (for example molecular oxygen, $O_3$ and ethylene) can modify the surface oxidation state of the lignocellulose material and its reactivity.

Acids and bases in the gaseous form can be used ($NH_3$, HCl, $SO_x$, $NO_x$, and the like).

Figure 3:
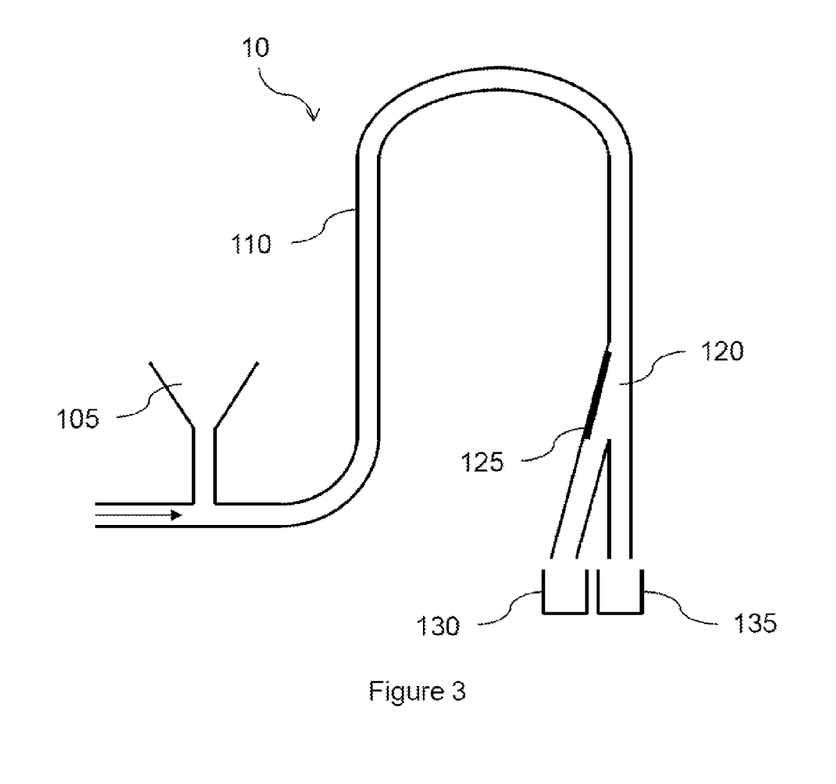
FIG. 3 represents, diagrammatically and in section, a first specific embodiment of the device which is a subject matter of the present invention.

A first embodiment of an electrostatic sorting device 100 is observed in FIG. 3. This device 100 comprises:
  an inlet 105 for ultrafine particles resulting from a grinding,
  a means 110 for triboelectrostatically charging the particles received and
  a main means 120 for electrostatic sorting of the conveyed particles.

The inlet 105 for ultrafine particles is, for example, a hopper or a funnel configured in order to make possible the pouring of a powder of ultrafine particles resulting from the grinding.

The particles thus poured into the inlet 105 for particles pass through a charging means 110 positioned, for example, under the inlet 105 for particles. This charging means 110 is configured in order for the particles to pass through this charging means 110 by virtue of gravitational force. In alternative forms, the movement of the particles is provided by a fluidized air bed system, that is to say an air bed system ventilated by virtue of a turbine or a fan. The triboelectrostatically charging is carried out by collision between the particles and the internal surface of a pipe. This surface comprises at least a portion made of polyvinyl chloride (abbreviation "PVC"). In alternative forms, this surface comprises at least a portion made of Teflon. In other alternative forms, this surface comprises at least a portion made of glass. In other alternative forms, this surface comprises at least a portion made of steel. PVC, Teflon, glass and steel have optimum properties for the charging of particles rich in lignocellulose. The charging means 110 is connected to the inlet of the sorting means 120.

The main means 120 for the electrostatic sorting of the conveyed particles comprises at least one electrode 125. This sorting means 120 is configured in order to sort the conveyed particles into fractions enriched in cellulose. This sorting is carried out by the use of the positively or negatively polarized electrode 125. Thus, the charged particles are attracted or repelled by the electrode 125. At the outlet of this main electrostatic sorting means 120, two pipes make it possible for the particles to pour out into two containers 130 and 135. The particles which have been attracted or repelled by the electrode 125, according to the polarization of the electrode 125, are poured out into a first container 130. The other particles are poured out into the second container 135.

In particular, the particles enriched in cellulose become charged with positive charges in the charging means 110. Consequently, these particles enriched in cellulose are attracted by a negatively polarized electrode. Thus, the particles pouring out into the pipe and then into the container 130 close to the negatively charged electrode comprise fractions enriched in cellulose. The particles rich in lignin-hemicelluloses and inorganics are attracted by the positive electrode and pour out into the container 135.

The ultrafine particles resulting from the grinding have the advantage of exhibiting a very homogeneous chemical composition. The triboelectrostatic charging means 110 makes it possible for the particles to become charged or discharged in electrons as a function of their main chemical component. The main electrostatic sorting means 120 thus separates the particles, the main components of which are different. The device 100 thus separates the fractions enriched in different components.

Figure 4:
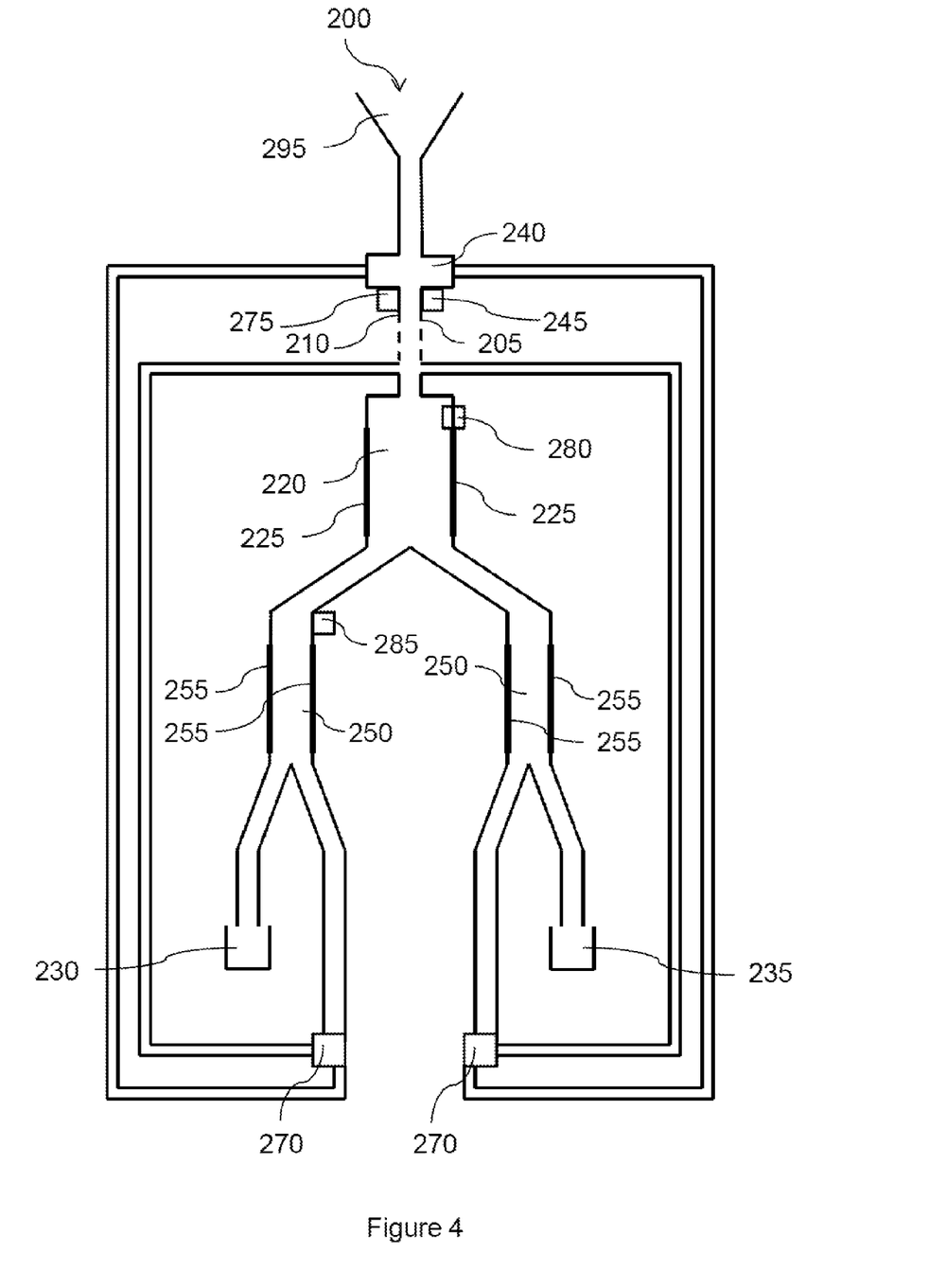
FIG. 4 represents, diagrammatically and in section, a second specific embodiment of the device which is a subject matter of the present invention.

A second specific embodiment of the device 200 which is a subject matter of the present invention is observed in FIG. 4. This device comprises:
  a means 240 for grinding the biomass to give a powder of ultrafine particles comprising:
    a means 245 for configuring the fineness of grinding carried out by the grinding means 240 and
    a means 275 for configuring the temperature of the grinding means 240;
  an inlet 205 for ultrafine particles resulting from a grinding,
  a means 210 for triboelectrostatically charging the particles received,
  a main means 220 for electrostatic sorting of the conveyed particles comprising:
    two electrodes 225;
    a means 280 for scraping an electrode of the main electrostatic sorting means 220 and
    a means 285 for reversing the polarity of an electrode 225 of the main electrostatic sorting means 220;
  two secondary electrostatic sorting means 250 each comprising two electrodes 255 and
  two means 270 for comparing the dimensions of particles compared with a predetermined limit value.

The means 240 for grinding the biomass to give a powder of ultrafine particles is, for example, a centrifugal mill configured so as to grind the biomass to give ultrafine particles. This grinding means 240 comprises a means 245 for configuring the fineness of the grinding carried out by the grinding means 240. This means 245 for configuring the fineness of the grinding is, for example, a touch screen on which a computer program displays the current grinding fineness, an interactive zone allowing a user to increase the grinding fineness and an interactive zone allowing the user to reduce the grinding fineness. Depending on the grinding fineness configured, the grinding means 240 is configured in order to grind the biomass into a powder of particles, the diameter of which has been defined by the configuration means 245. This grinding means 240 also comprises a means 275 for configuring the temperature of the grinding means 240. This means 275 for configuring the temperature is, for example, a touch screen on which a computer program displays the current temperature of the grinding means 240, an interactive zone allowing a user to increase said temperature and an interactive zone allowing the user to reduce said temperature.

The inlet 205 for ultrafine particles resulting from a grinding is, for example, a pipe connecting the grinding means 240 and the means 210 for triboelectrostatically charging the particles received.

The means 210 for triboelectrostatic charging of the particles received is, for example, an internal surface of a pipe, at least a portion of which is made of glass, Teflon, PVC or steel. The particles running through the pipe become charged on contact with the charging means 210. In particular, the cellulose becomes charged with positive charges.

The particles move in the charging means 210 by virtue of the use of a dynamic fluidized air bed set in motion by a turbine, for example.

The main means 220 for electrostatic sorting of the conveyed particles is, for example, a cylindrical pipe, on the internal surface of which are placed two diametrically opposed electrodes 225. One of these electrodes 225 is positively polarized and the other electrode 225 is negatively polarized. Two pipes, configured so as to allow the passage of the particles which are attracted by one or other of the electrodes 225, are positioned close to each of these electrodes 225 and downstream of the sorting means 220. The particles negatively charged by the charging means 210 are attracted by the positively charged electrode 225. The particles positively charged by the charging means 210 are attracted by the negatively charged electrode 225.

This main electrostatic sorting means 220 additionally comprises a means 280 for scraping an electrode of the main electrostatic sorting means 220. This scraping means 280 is, for example a form made of flexible plastic configured in order to match the shapes of the electrode 225 on which the form is placed. This form is set in motion by a mechanical motor when the device is shut down.

This scraping means 280 is configured in order to collect the particles thus scraped off. The particles scraped off have the distinguishing feature of comprising a large number of fractions attracted by the electrode 225, so much so that these particles become attached to the electrode 225. For example, in the case of a negatively charged electrode 225, the particles collected by the scraping means 280 predominantly comprise fractions comprising cellulose.

This main electrostatic sorting means 220 additionally comprises a means 285 for reversing the polarity of an electrode 225 of the main electrostatic sorting means 220. This means for reversing the polarity is, for example, an electronic circuit, employed a tenth of a second every minute, configured in order to reverse the polarity of the electrode 225. The inversion of polarity makes it possible to detach and collect the particles attached to said electrode 225.

In alternative forms, the main electrostatic sorting means 220 comprises a scraping means 280 and a means 285 for reversing the polarity for each electrode 225 of the sorting means 220.

A secondary electrostatic sorting means 250 is positioned at the end of each of the pipes of the main electrostatic sorting means 220. Each of these secondary electrostatic sorting means 250 comprises a positively or negatively polarized electrode. The electrode of the secondary sorting means 250 is polarized similarly to the electrode close to the pipe to which said secondary sorting means 250 is attached.

In alternative forms, the electrode of the secondary sorting means 250 is polarized in reverse manner to the electrode close to the pipe to which said secondary sorting means 250 is attached.

In alternative forms, at least one secondary electrostatic sorting means 250 comprises two oppositely polarized electrodes located on either side of said secondary sorting means 250. In this way, the particles comprising a majority of fractions comprising lignocellulose are attracted by one of the electrodes. Each secondary electrostatic sorting means 250 thus makes it possible to sort the particles comprising, on the one hand, a majority of cellulose and, on the other hand, a majority of lignin-hemicelluloses and inorganics.

Two pipes are positioned at the outlet of each secondary sorting means 250. A first pipe corresponds to a similar sorting result, said to be "convergent", by the first sorting means 220 and the secondary sorting means 250 at the outlet of which this pipe is positioned. For example, a particle comprising a high proportion of cellulose is positively charged, then attracted by the negatively charged electrode in the sorting means 220 and then finally attracted by the negatively charged electrode in the secondary sorting means 250. In the case where the result of the sorting of a particle by the sorting means 220 and the secondary sorting means 250 is different, the result of the sorting is said to "diverge". In the case where the result of the sorting by the sorting means 220 and the secondary sorting means 250 diverges, the particle enters the second pipe at the outlet of said secondary sorting means 250.

In alternative forms, at least one secondary sorting means 250 comprises at least one scraping means 280 and/or one means 285 for reversing polarity which is similar to those configured for the main electrostatic sorting means 220.

Each pipe configured in order to receive the particles, the result of the sorting of which by the sorting means 220 and the secondary sorting means 250 diverges, comprises a means 270 for comparing the dimensions of particles compared with a predetermined limit value. This comparing means 270 is, for example, a sorter of cyclone type. In alternative forms, this comparing means 270 is a filter configured in order to retain the particles, the dimensions of which are greater than the predetermined limit value.

The particles, the dimensions of which are greater than the predetermined limit value, are conveyed to the grinding means 240 in order to be ground again.

The particles, the dimensions of which are lower than the predetermined limit value, are conveyed again to the charging means 210 in order to be sorted.

The ultrafine particles resulting from the grinding have the advantage of exhibiting a very homogeneous chemical composition. The triboelectrostatically charging means 210 make it possible for the particles to be charged or to be discharged in electrons as a function of their main component. The main electrostatic sorting means 220 thus separates the particles, the main components of which are different. The device 200 thus separates the fractions of the biomass enriched in different components, these components having different properties and different industrial applications.

Figure 5:
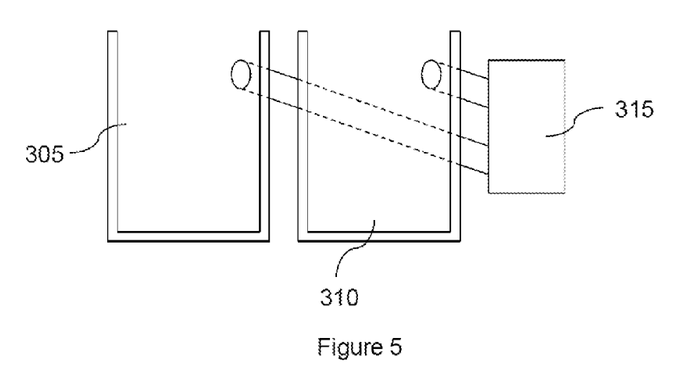
FIG. 5 represents, diagrammatically and in section, a portion of one of the embodiments illustrated in FIGS. 3 and 4.

Furthermore, the separation of the components resulting from the plurality of successive sortings carried out by the main sorting means 220 and the two secondary sorting means 250 of the device 200 is then more precise than if the device 200 comprised just one main electrostatic sorting means 220, as in the device 100 illustrated in FIG. 5.

The device 200 concentrates the grinding means 240, the receiving means 205, the charging means 210 and each sorting means 220, 250. Thus, the device 200 is more compact. Furthermore, the powder does not have the time to become aggregated, to become charged with moisture, to become oxidized or more generally to change state, between the grinding and the sorting. The operation of the device is thereby improved.

The main diameter of the particles at the outlet of the grinding means 240 of the device 200 makes it possible to obtain particles which:
have a homogeneous chemical composition and
once charged, remain mobile as a function of their charge in the presence of the electrodes.

By virtue of the comparing means 270 of the device 200, the particles which are too large to be efficiently sorted are ground again so as to optimize the sorting of these particles. On the other hand, the particles, the dimensions of which are nominal, can be resorted without further grinding.

The means 275 for configuring the temperature of the grinding means 240 configured in order for the biomass to reach a temperature at which at least one component of the biomass becomes brittle makes it possible for the grinding means 240 to more easily grind the biomass to give ultrafine particles.

The use of a fluidized air bed makes possible simultaneously the formation of the electrostatic charges on the moving particles and their separation for the purpose of their sorting.

The means 280 for scraping an electrode 225 of the main electrostatic sorting means 220 makes it possible to collect the particles attached to the electrode 225, the electric charge of which is high, which means that their composition is particularly homogeneous.

The means 285 for cyclically reversing the polarity of each electrode 225 of the main electrostatic sorting means 220 makes it possible to detach the particles attached to the electrodes 225, the compositions of which are particularly homogeneous, and to collect the particles attached to each electrode without a mechanical action, such as scraping.

Figure 7:
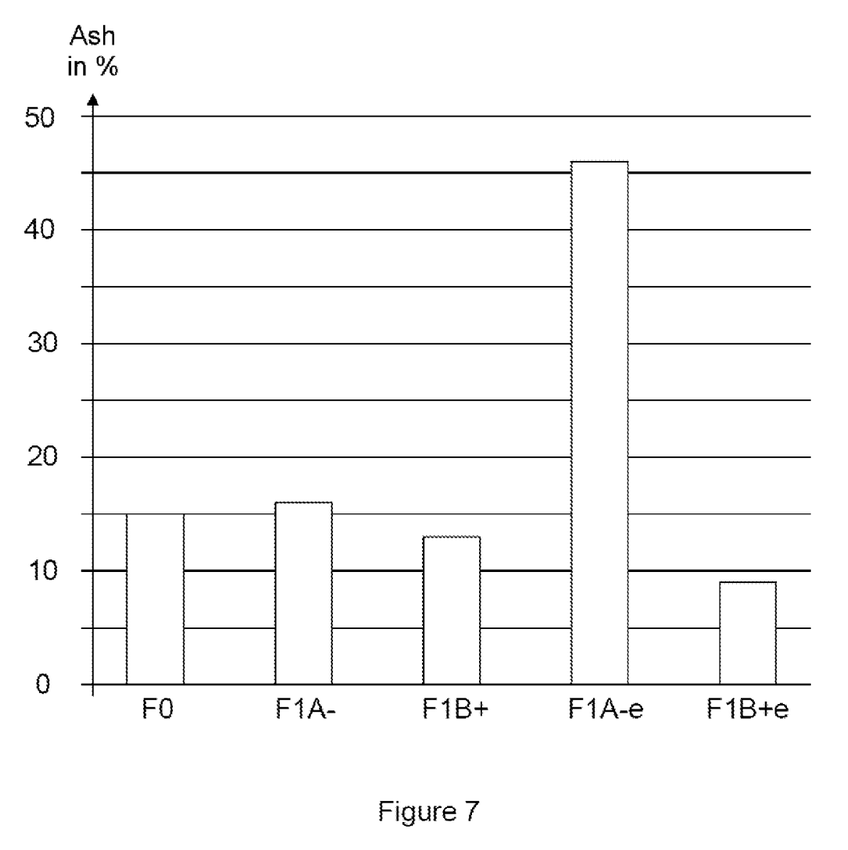
FIG. 7 represents, in the form of a histogram, ash contents of fractions obtained by the implementation of the process which is a subject matter of the present invention on rice hulls.

Two cyclonic separation units 305 and 310 connected to the same single suction means 315 are observed in FIG. 7. It should be remembered that a cyclonic separation unit is a technological unit which applies a rapid rotation on a gas in order to separate therefrom, by centrifuging, the fine solid particles which are mixed therein. The inlets of the cyclonic separation units 305 and 310 respectively constitute the containers 130 or 230, on the one hand, and 135 or 235, on the other hand.

Exemplary Embodiments and Results Obtained with the Process

In the tables of results below:
F0 represents the initial sample,
F1B+ represents the fraction obtained on the positively charged electrode when just one stage is carried out,
F1A− represents the fraction obtained on the negatively charged electrode when just one stage is carried out,
F2B+ represents the fraction obtained on the positively charged electrode when, at the inlet of a second stage, the sample is the fraction F1B+,
F2A− represents the fraction obtained on the negatively charged electrode when, at the inlet of a second stage, the sample is the fraction F1A− and
the ending of the name of the fraction with "e" means that the fraction has been obtained by scraping of the electrode.

EXAMPLE 1

Application of the Process which is a Subject Matter of the Present Invention to Wheat Straw As regards the method of preparation, a crude wheat straw sample was subjected to the following refining operations:
impregnation (without treatment),
no drying operation and
grinding.

The wheat straw was ground without preliminary treatment with a moisture content of less than 20% (by weight). The grinder used is an impact mill for particle sizes of less than 200 μm. The substrates are ground beforehand in a knife mill and then in a centrifugal mill.

The different ground products or powders obtained were separated by electrostatic sorting under the following conditions:
the feeding rate is from 0.5 to 1 kg/h and
the voltage is from 5 to 20 kV.

The different fractions obtained are characterized and a characterization example is presented in Table 1 (the tribo-electrostatic sorting is carried out with electrodes exhibiting a difference in potential of 15 kvolts, at a distance, between them, of 3 cm, and measuring 30 cm in height for 10 cm in width).

TABLE 1

Example of wheat straw - Composition of fractions, by weight

| Fractions | Content recovered | $d_{50\ (\mu m)}$ | Ash | Lignin | Hemi-celluloses | Cellulose |
|---|---|---|---|---|---|---|
| F0 | | 81.9 | 4.43 | 20.5 | 28.3 | 44.2 |
| F1A− | 25 | 81.2 | 5.14 | 22.4 | 32.5 | 41.8 |
| F1B+ | 46 | 52.2 | 3.67 | 18.1 | 22.6 | 54.7 |
| F1A−e | 4 | 42.2 | 15.2 | 16.6 | 30.1 | 37.3 |
| F1B+e | 5 | 44.8 | 2.94 | 16.6 | 22.4 | 57.8 |

The content recovered (second column) is given as percentage by weight.

It is observed that the combination of the operations of grinding of the wheat straw and of electrostatic sorting in a strict dry medium has made it possible to isolate:
on the one hand, fractions enriched in cellulose (up to 57.8%, compared to 44.2% in the crude straw) and depleted in hemicelluloses (down to 22.4%, compared with 28.3% in the crude straw) and
on the other hand, fractions enriched in lignin (up to 22.4%, compared with 20.5% in the crude straw), hemicelluloses (up to 32.5%, compared with 28.3% in the crude straw) or lignin-hemicelluloses complexes.

Fractions have also been obtained, on the electrodes, which are very rich in inorganics (up to 15.2% for the fraction F1A−, compared with 4.4% in the crude straw), without chemical modifications.

It is observed, in the light of this table 1, that the fractions F1B+ and F1B+e contain more cellulose, in comparison with the other fractions. This cellulose can be used as bioenergy source after hydrolysis into glucose and fermentation (bioethanol and biogas). On the other hand, the fractions F1A− and F1A−e are enriched in lignin-hemicelluloses, which may be intended for the synthesis of biobased materials.

Thus, the bioaccessibility and the conversion of the cellulose into glucose (with a doubled content compared with the crude straw) have been improved, without having recourse to chemical pretreatments. Fractions enriched in lignin-hemicelluloses complexes and in inorganics which may be intended for the synthesis of biobased materials have been concentrated.

Figure 6:
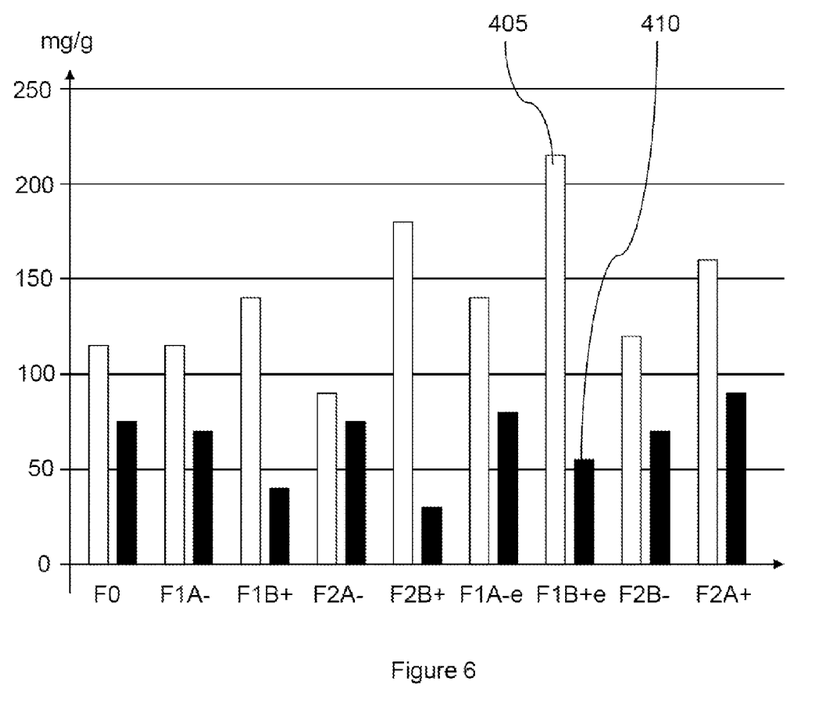
FIG. 6 represents, in the form of a histogram, an enzymatic hydrolysis of wheat straw fractions resulting from the electrostatic sorting.

FIG. 6 illustrates the conversion by enzymatic hydrolysis of the wheat straw fractions, as described in the publication Barakat et al., "Eco-friendly dry chemo-mechanical pretreatments of lignocellulosic biomass: impact on energy and yield of the enzymatic hydrolysis", Applied Energy, 2014, 113 (2014), 97-105, incorporated herein by reference, which describes in detail the methods used here to analyze the sugars, lignin and enzymatic purification.

The white vertical bars represent, in mg/g, the glucose (cellulose). The black vertical bars represent, in mg/g, the xylose (hemicelluloses). This FIG. 6 demonstrates the enriching in hydrolysable cellulose in the "+" fractions. The glucose resulting from the enzymatic hydrolysis of the cellulose can be used as source of fermentation for the production of bioethanol or of other molecules intended for green chemistry, depending on the fermentive microorganisms used.

EXAMPLE 2

Rice Hull

In the case of rice hull, a crude rice hull sample was subjected to the following operations:
  grinding with a knife mill,
  grinding with a blade mill,
  drying down to a water content of less than 10%,
  grinding with a rotary ball mill and
  electrostatic sorting in two passes.

FIG. 7 gives the contents of fractions obtained by the use of the process which is a subject matter of the present invention on rice hulls, as percentage by weight, and the ash content of some of these fractions.

The following are thus separated, starting from rice hulls:
  a fraction enriched in inorganics and in particular in silica and
  a fraction enriched in lignin and cellulose and depleted in inorganics.

The fraction enriched in inorganics and in silica can be used for the implementation of biobased materials (concretes, for example).

The fraction enriched in lignin and cellulose and depleted in inorganics can be used for fuel applications.

EXAMPLE 3

Rice Straw

Figure 8:
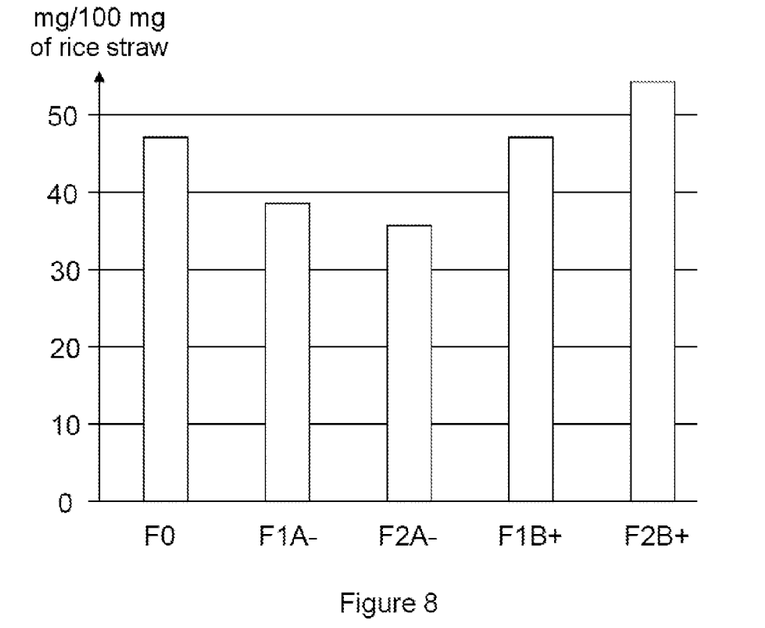
FIG. 8 represents, in the form of a histogram, cellulose contents of fractions obtained by the implementation of the process which is a subject matter of the present invention on rice straw.
Figure 9:
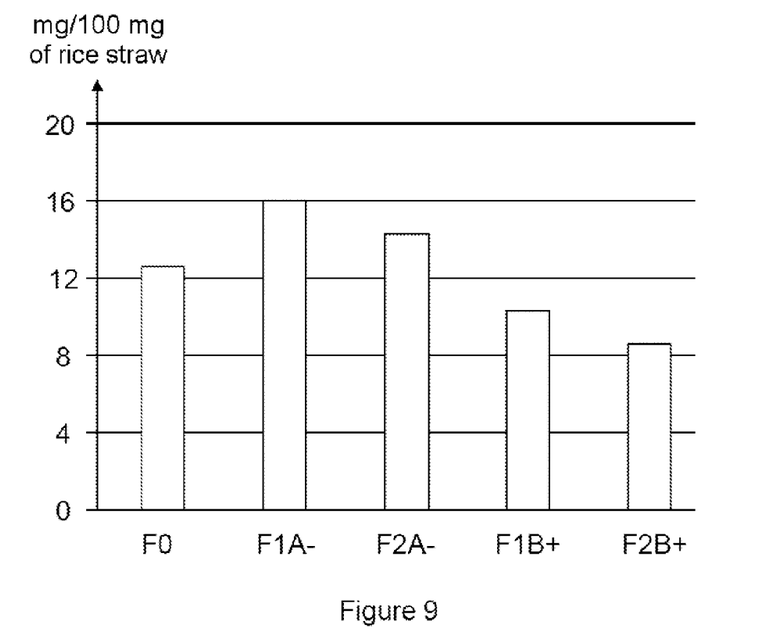
FIG. 9 represents, in the form of a histogram, lignin contents of fractions obtained by the implementation of the process which is a subject matter of the present invention on rice straw.

FIGS. 8 and 9 respectively represent the contents of cellulose and of lignin of different fractions obtained by the use of the process which is a subject matter of the present invention on a biomass consisting of rice straw.

It is observed that this process makes it possible to obtain:
  on the one hand, fractions enriched in cellulose (F1B+ and F2B+) and
  on the other hand, fractions enriched in lignin (F1A− and F2A−).

EXAMPLE 4

Wheat Straw

The grinding step which has the greatest energy cost is the final grinding step, which brings the particle size within the ultrafine range (from one hundredth to a tenth of a micrometer). It is thus with regard to the latter that the efforts targeted at reducing the grinding energy are to be directed. The following example is given with regard to wheat straw, with a laboratory rotary ball mill.

The temperature inside the grinding jar (Marne 0 ball mill from Faure Instruments) can reach 40° C. when the grinding is carried out at ambient temperature, which has an effect on the elasticity/stiffness of the straw fibers. In order to limit this effect of loss of stiffness, the ball mill was used in a cold chamber at 5° C. (the inside of the mill then rises to 20° C. in stabilized operation).

FIG. 10 shows the change in the grinding time as a function of the temperature: the total grinding time in order to get back to a $d_{50}$ of 20 μm is 120 hours at 40° C. (top curve) versus 70 hours at 20° C. (bottom curve).

The fragmentability of the biomass is improved by the use of low temperatures: it is necessary to control the grinding temperature in order to keep the plants within their stiffness range, i.e. under 40° C. for the materials considered. Highly negative temperatures do not contribute a real advantage (high cost, reagglomeration and reabsorption of moisture by condensation during the return to ambient temperature).

EXAMPLE 5

Wheat Straw

In order to observe an effect of the grinding atmosphere on the grindability and/or on the reactivity of the wheat straw, tests were carried out in an oxidizing atmosphere (air) and in a neutral atmosphere (argon) in a Faure Marne 0 model ball mill provided with an 8 liter ceramic jar.

The presence of argon during the grinding does not affect the fragmentability of the wheat straw. The time necessary to obtain a 20 micron powder is the same. On the other hand, the reactivity, for example the ability to release thermal energy, is modified.

EXAMPLE 6

Wheat Straw

A combination of an electrostatic separation and of a chemical pretreatment and of an enzymatic treatment subsequent to the separation is described below.

Figure 11:
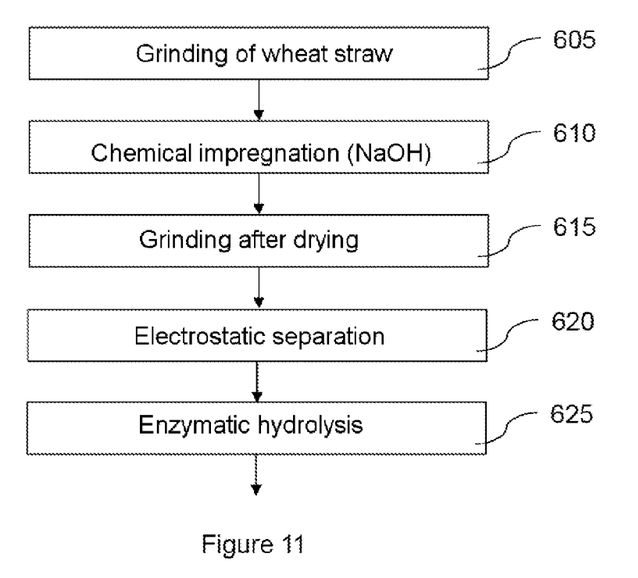
FIG. 11 represents, in the form of a logic diagram, steps of a specific embodiment of the process which is a subject matter of the present invention comprising a pretreatment of the biomass and a treatment of at least one enriched fraction.

As illustrated in FIG. 11, during a step 605, the wheat straw is ground, for example using a knife mill with a 2 mm screen. The ground straw is then impregnated with sodium hydroxide during a step 610. For example, this step 610 is carried out according to the method described by Barakat et al., 2014, in the publication referenced above.

After drying at 40° C. until the moisture content reaches a value between 7% and 10%, the biomass is again ground with an impact mill (UPZ, already described in detail with regard to FIGS. 1 to 9) during a step 615. The ground product is subsequently fractionated by electrostatic separation according to the same method and under the conditions described with regard to FIGS. 1 to 9, during a step 620.

During a step 625, at least one of the enriched fractions thus obtained is functionalized by treatment with enzymes (Barakat et al., 2014).

Figure 12:
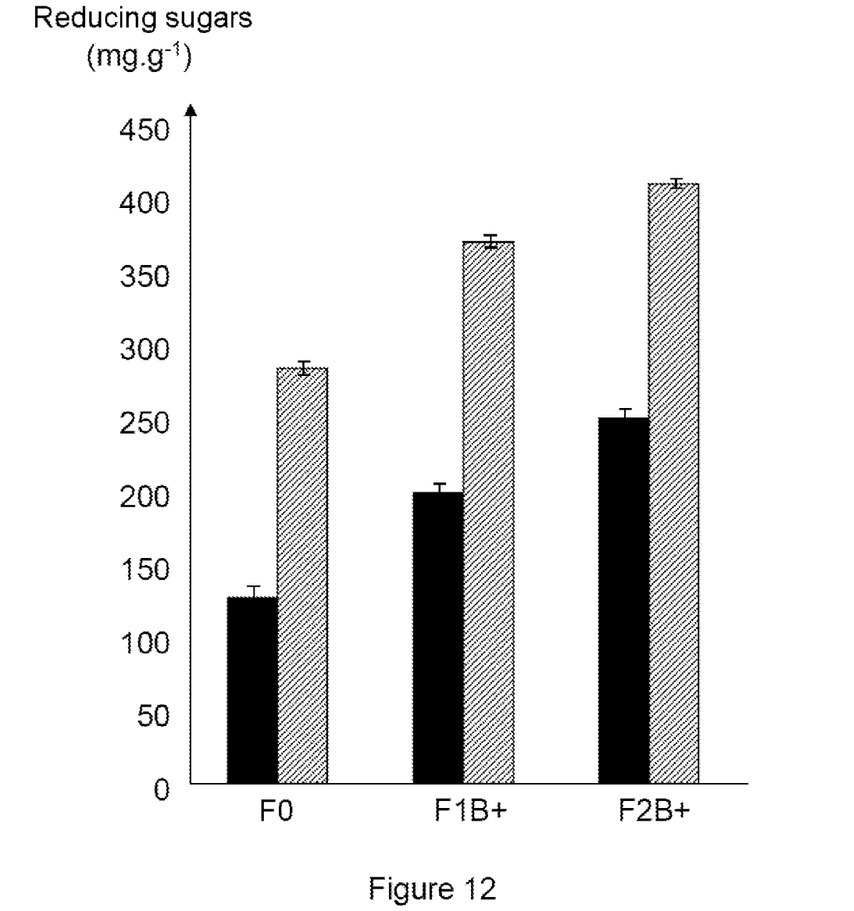
FIG. 12 represents contents of reducing sugars obtained by carrying out the process illustrated in FIG. 11.

The results obtained are presented in FIG. 12. The ordinate y represents the content of reducing sugars (glucose), in milligrams per gram.

The unseparated straw is represented on the left. The positive fractions F1B+ after one pass through the separator are represented in the center. The positive fractions F2B+ after two passes through the separator are represented on the right. The solid black rectangles represent the results obtained in the absence of impregnation with sodium hydroxide. The hatched rectangles represent the results obtained with a step of impregnation with sodium hydroxide.

In general, the coupling of the chemical treatment, grinding and electrostatic separation processes has a very significant effect on the accessibility of the cellulose by the enzymes (cellulases) and the production of glucose (precursor for producing ethanol), which achieves a yield of 95% for the positively charged fractions.

The invention claimed is:

1. A dry process for the fractionation of lignocellulosic biomass comprising at least 50% by weight of lignins, cellulose and hemicelluloses, comprising the steps of:
    fragmenting the biomass to obtain an ultrafine powder; and
    at least one step of separating a fraction enriched in cellulose, on the one hand, and a fraction enriched in lignin, hemicelluloses and inorganics, on the other hand, by electrostatic sorting of ultrafine particles.

2. The process as claimed in claim 1, wherein the step of separating the fractions comprises the steps of:
    triboelectrostatically charging the ultrafine particles; and
    at least one step of deviating a path of the particles in an electric field to sort the particles.

3. The process as claimed in claim 2, further comprising the step of scraping an electrode of an electrostatic sorter used during the deviating step to collect the charged particles attached to the electrode after the deviating step.

4. The process as claimed in claim 2, further comprising the step of cyclically reversing a polarity of each electrode of an electrostatic sorter used during the deviating step.

5. The process as claimed in claim 2, further comprising, downstream of the deviating step, at least one secondary deviating step.

6. The process as claimed in claim 2, further comprising the steps of, downstream of the deviating step, comparing sizes of the particles with a predetermined limit value; and feeding a grinder with the particles, the sizes of which are greater than the predetermined limit value.

7. The process as claimed in claim 2, wherein a dynamic fluidized air bed is used during the triboelectrostatically charging step.

8. The process as claimed in claim 1, wherein the step of fragmenting the biomass comprises the step of grinding of the biomass.

9. The process as claimed in claim 8, wherein a vibrating mill or a rotary ball mill is utilized during the step of fragmenting the biomass.

10. The process as claimed in claim 1, further comprising the step of pre-treating the biomass upstream of or during the step of fragmenting the biomass.

11. The process as claimed in claim 10, wherein a chemical treatment of the biomass is carried out by contact with an oxidizing gas or aerosol during the pretreatment step.

12. The process as claimed in claim 10, wherein a chemical treatment of the biomass is carried out by contact with a reducing gas or aerosol during the pretreatment step.

13. The process as claimed in claim 10, wherein the biomass is treated with an inert gas during the pretreatment step.

14. The process as claimed in claim 13, wherein the inert gas is chosen from nitrogen, argon and carbon dioxide $CO_2$.

15. The process as claimed in claim 1, further comprising the step of functionalizing at least one enriched fraction downstream of the separating step.

16. The process as claimed in claim 15, wherein the enriched fraction is roasted during the functionalizing step.

17. The process as claimed in claim 15, wherein an enzymatic hydrolysis of the enriched fraction is carried out during the functionalizing step.

18. A method of generating biofuel using the process as claimed in claim 1, said method comprising a step of generating biofuel from the fraction enriched in cellulose or fraction enriched in lignin, hemicelluloses and inorganics obtained by the process.

19. A method of producing bio-based materials using the process as claimed in claim 1, said method comprising a step of producing bio-based materials from the fraction enriched in the cellulose or the fraction enriched in lignin, hemicellulose and inorganics obtained by the process.

* * * * *